United States Patent [19]
Yamaguchi et al.

[11] Patent Number: 4,981,570
[45] Date of Patent: Jan. 1, 1991

[54] ION CARRIER MEMBRANE, AND ION SENSOR HAVING SAME

[75] Inventors: Shuichiro Yamaguchi; Takanao Suzuki; Norio Daikuhara; Takeshi Shimomura, all of Fuji; Noboru Oyama, Tokyo, all of Japan

[73] Assignee: Terumo Kabushiki Kaisha, Tokyo, Japan

[21] Appl. No.: 378,233
[22] PCT Filed: Dec. 10, 1987
[86] PCT No.: PCT/JP87/00962
  § 371 Date: Aug. 7, 1989
  § 102(e) Date: Aug. 7, 1989
[87] PCT Pub. No.: WO88/04425
  PCT Pub. Date: Jun. 16, 1988

[30] Foreign Application Priority Data
  Dec. 10, 1986 [JP] Japan .................. 61-292291
  Jan. 28, 1987 [JP] Japan .................. 62-015950
  Jan. 28, 1987 [JP] Japan .................. 62-015951

[51] Int. Cl.$^5$ ........................... G01N 27/333
[52] U.S. Cl. ........................... 204/418; 357/25
[58] Field of Search ..................... 204/418; 357/25

[56] References Cited
U.S. PATENT DOCUMENTS

| | | | |
|---|---|---|---|
| 3,598,713 | 8/1971 | Baum et al. | 204/417 |
| 3,926,764 | 12/1975 | Ruzicka et al. | 204/418 |
| 3,932,233 | 1/1976 | Ruzicka et al. | 204/418 |
| 3,957,612 | 5/1976 | Niedrach et al. | 204/414 |
| 3,957,613 | 5/1976 | Macur | 204/412 |
| 4,052,285 | 10/1977 | Dobson | 204/418 |
| 4,115,209 | 9/1978 | Fraiser et al. | 204/153.1 |
| 4,198,851 | 4/1980 | Janata | 73/31.06 |
| 4,214,968 | 7/1980 | Battaglia et al. | 204/418 |
| 4,271,002 | 6/1981 | Hawkins | 204/418 |
| 4,280,889 | 7/1981 | Szonntagh | 204/408 |
| 4,282,079 | 8/1981 | Chang et al. | 204/420 |
| 4,305,802 | 12/1981 | Koshiishi | 204/418 |
| 4,454,007 | 6/1984 | Pace | 204/153.1 |
| 4,512,870 | 4/1985 | Kohara et al. | 204/416 |
| 4,549,951 | 10/1985 | Knudson et al. | 204/416 |
| 4,561,962 | 12/1985 | Kankare | 204/415 |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/153.1 |
| 4,753,719 | 6/1988 | Yamaguchi et al. | 204/418 |
| 4,798,664 | 1/1989 | Yamaguchi et al. | 204/418 |
| 4,816,118 | 3/1989 | Oyama et al. | 204/418 |
| 4,839,020 | 6/1989 | Yamaguchi et al. | 204/431 |
| 4,861,454 | 8/1989 | Ushizawa et al. | 204/414 |

OTHER PUBLICATIONS

Patent Abstracts of Japan, vol. 9, No. 122, May 28, 1985, Japanese Kokai No. 60-7357.
Patent Abstracts of Japan, vol. 7, No. 48 (p. 178), Feb. 24, 1983, Japanese Kokai No. 57-196,116.
Oyama et al., "Electrochemical Properties of Electropolymerized Poly (1-pyrinamine Films)", Bull Chem. Soc., Japan 59-2071-2080, 1986.
Ryan, "Electrochemical Detectors Fundamental Aspects and Analytical Applications", Plenum Press, Apr. 26, 1985, p. 7.

(List continued on next page.)

Primary Examiner—G. L. Kaplan
Attorney, Agent, or Firm—Burns, Doane, Swecker & Mathis

[57] ABSTRACT

The surface of an electrically conductive substrate (1) is provided with a redox layer (5) by an electrolytic polymerization process, and the surface of the resulting member is further provided with an ion carrier membrane (6) which includes polyvinyl chloride, a plasticizer and an ion carrier, thereby forming an ion sensor. Used as the plasticizer is one selected from among phthalate plasticizers, maleate plasticizers, adipate plasticizers, carboxylate plasticizers and polycaprolactone plasticizers, or one selected from among plasticizers comprising modified ethylene - vinyl acetate copolymer. The ion sensor obtained has low solubility in the plasticizer of the redox layer and therefore is highly stable. Since the ion sensor has little toxicity, it can be used in vivo. A preferred plasticizer is benzopohenontetracarboxylic under cyclic acid.

3 Claims, 8 Drawing Sheets

OTHER PUBLICATIONS

Ma et al., "Organic Analysis Using Ion-Sensitive electrodes", Academic Press, 1982, pp. 62 & 70.

Ammann, "Ion Selective Microelectrodes", Springer-Verlag, N.Y., pp. 5-7 & 6.

Wuthier et al. "Tin Organic Compounds as Neutral Carriers for Anion Selective Electrodes", Analytical Chem. vol. 56, No. 3, 3/84, pp. 535-538.

Norov et al. "Calcium-Selective Electrode Without an Internal Reference Solution", Journal of Analytical Chemistry, vol. 34, No. 8, Part 1, Aug. 1979, pp. 1139-1162.

Oyama, "Ion Selective Microelectrode Prepared by Modifying an Electrode with Polymers ", Int. Electrical Symposium, Schaumberg, IL, May 27-29, 1987, pp. 122-125.

Oyama et al., "A New Type of Ion-Selective Microelectrodes Using Electropolymerized Thin Films", j-4 Bioelectroanalytical Chemistry Symposium, Honolulu, HA, Oct. 18-23, 1987.

Oyama et al., "Ion Selective Electrode Prepared by Modifying an Electrode with Polymers", Tokyo Seminar on Macromolecular Complexes, Tokyo, Univ. Oct. 14-18, 1987.

Urs Oesch et al., Anal. chem. 52(4) 692-700 (1980).

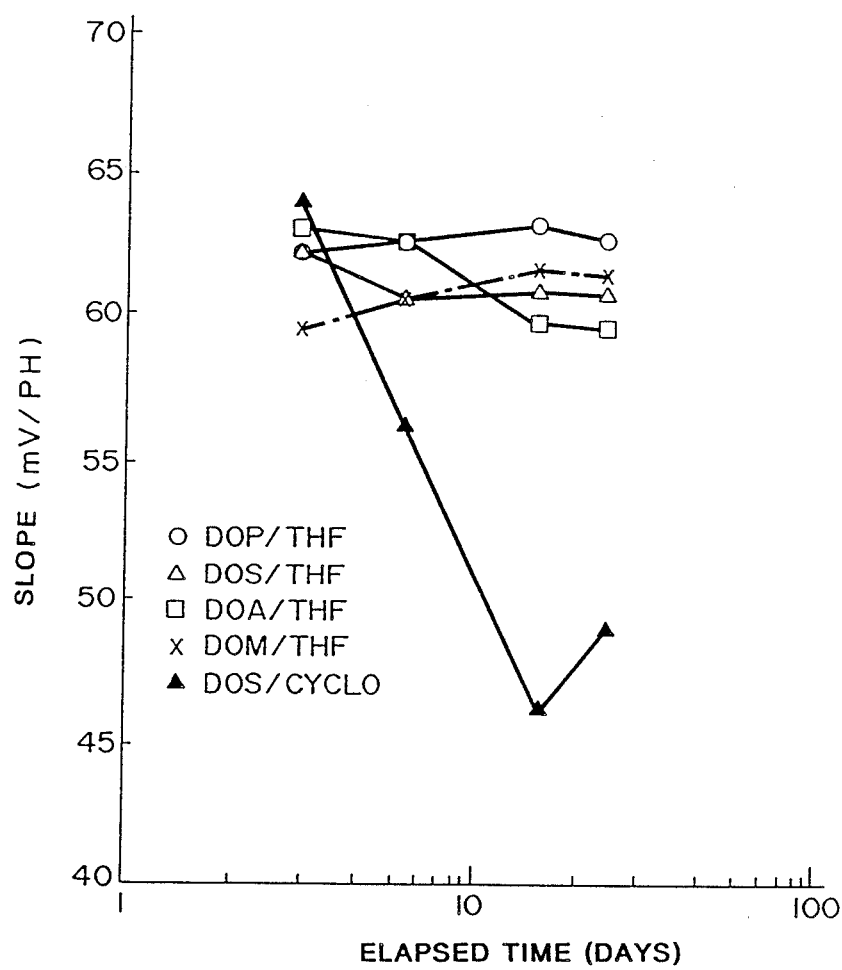
F I G. 3(b)

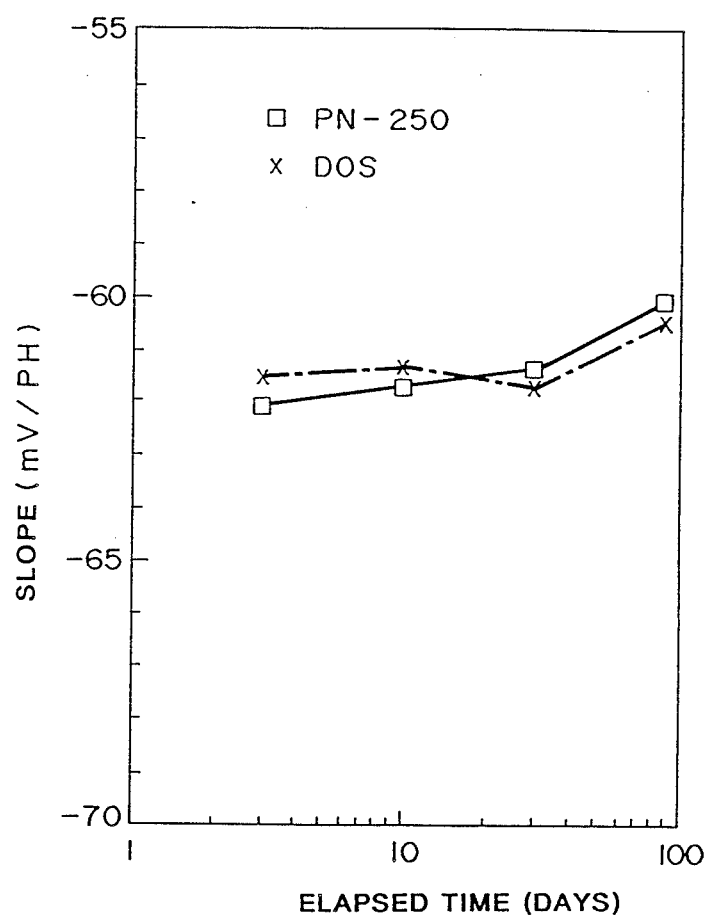
F I G. 6(a)

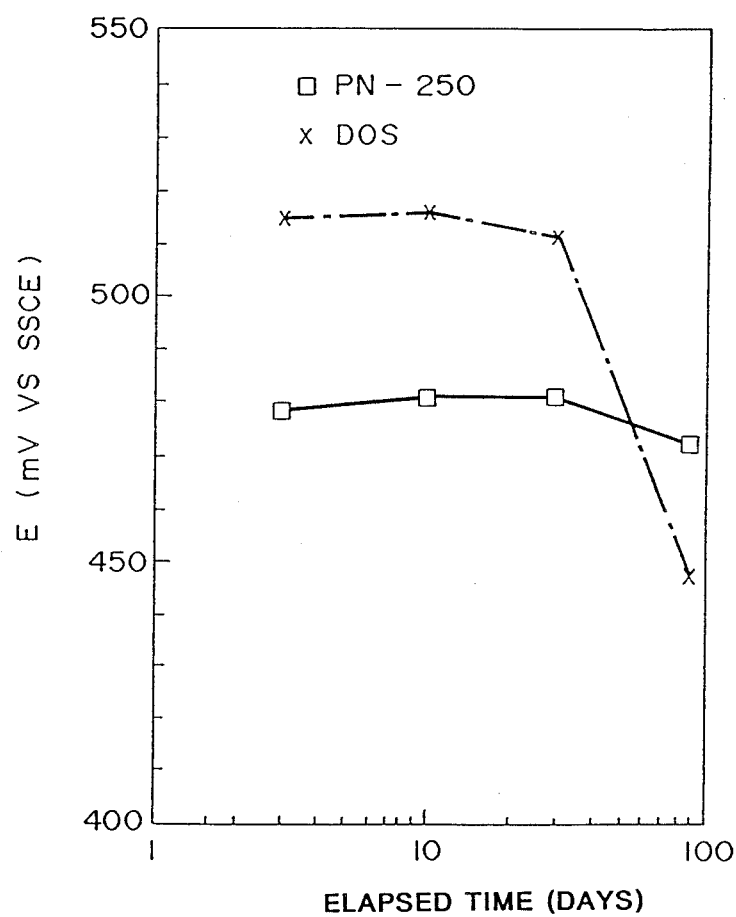
F I G. 6(b)

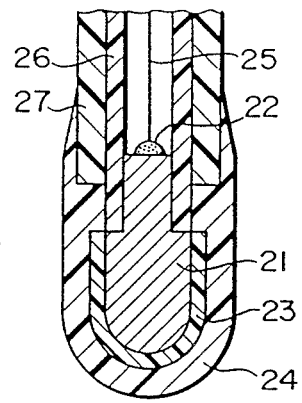
F I G. 7
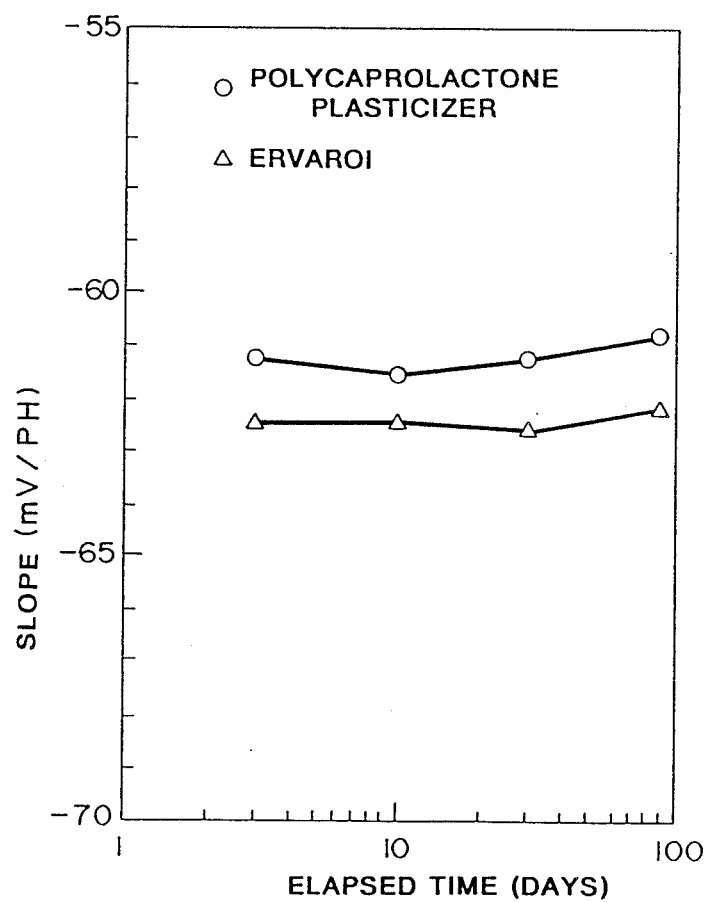
F I G. 8(a)

ION CARRIER MEMBRANE, AND ION SENSOR HAVING SAME

TECHNICAL FIELD

This invention relates to an ion carrier membrane. More particularly, the invention relates to an ion carrier membrane which exhibits ion selectivity in an ion sensor, ion-selective FET sensor (ISFET) and the like, and to an ion sensor equipped with such an ion carrier membrane.

BACKGROUND ART

With regard to the action of a plasticizer in the membrane composition of a polymeric ion carrier membrane in a liquid membrane-type electrode of an ion sensor or the like in which the polymeric membrane is substituted for a glass membrane, W. Simon et al have found that the dielectric constant of the membrane solution (plasticizer) (a water-immiscible liquid of low vapor pressure, compatible with PVC, no functional group of which can undergo protonation reaction) enhances the selectivity of a monovalent cation of the same size ["Ion Enzyme Electrodes in Biology & Medicine", W. Simon, Int. Workshop, pp. 22-37 (1976)]. As a result, o-NPOE [o-nitrophenyl-n-octylether 24 (20° C.)] is used as the plasticizer, and this is put to use in an Na$^+$ sensor and K$^+$ sensor. It was subsequently reported that DOS (dioctyl sebacate), which has a high lipophilic/hydrophilic distribution coefficient, is best suited for an ion-selective electrode [Anal. Chemistry 52 (4) 692-700 (1980)]. However, this concept does not hold true in a case where the ion carrier membrane is of a solid-state type. In such case, the stability between the ion carrier membrane and an electrolytic polymeric membrane takes on great importance.

In the prior art, it is known to incorporate an ion carrier substance in the ion carrier membrane used in an ion-selective electrode, in which a polyvinyl chloride resin serves as a matrix and a plasticizer serves as the solvent. Examples of the plasticizer which can be used are phthalate esters, maleates, sebacates and adipates, though flow-out of these plasticizers and the toxicity of the effluent pose problems. In particular, it is known that the amount of plasticizer outflow increases in blood or body fluids. For this reason, a plasticizer which exhibits little outflow is desirable as the membrane for an ion sensor of the type used to subject blood or body fluids to measurement.

In Japanese Patent Application Laid-Open Nos. 61-155949 and 61-194343, etc., the inventors have previously reported on an ion sensor obtained by depositing a redox layer on an electrically conductive substrate, and coating the result with an ion carrier membrane. From the standpoint of durability, it is desired that the plasticizer in these ion carrier membranes have little solubility with respect to the redox layer composition.

DISCLOSURE OF THE INVENTION

The present invention provides an ion carrier membrane and an ion sensor having the same, which ion carrier membrane improves the stability between itself and an electrolytic polymeric membrane through use of a plasticizer which does not readily dissolve in a solution and which exhibits ionic mobility in the ion carrier membrane.

Further, the present invention provides an ion carrier membrane and an ion sensor having the same, which ion carrier membrane reduces the outflow of materials to blood or the like and raises the durability of the ion sensor through use of a plasticizer which does not readily dissolve in a solution under measurement and which exhibits little mutual solubility with respect to an electrolytic polymeric membrane (redox layer).

As means for solving the foregoing problems, the ion carrier membrane of the invention is an ion carrier membrane sensitive to a prescribed ion and comprising polyvinyl chloride plasticized by a plasticizer, the plasticizer being selected from at least one of maleate plasticizers, and carboxylate plasticizers.

Further, the ion carrier membrane of the invention is an ion carrier membrane sensitive to a prescribed ion and comprising polyvinyl chloride plasticized by a plasticizer, the plasticizer being selected from polycaprolactone plasticizers and plasticizers comprising modified ethylene—vinyl acetate copolymer.

Further, an ion sensor according to the invention comprises an electrically conductive substrate, a redox layer exhibiting a redox function coating the electrically conductive substrate, and an ion carrier membrane coating the redox layer, wherein the ion carrier membrane is sensitive to a prescribed ion and comprises polyvinyl chloride plasticized by a plasticizer, the plasticizer being selected from at least one of phthalate plasticizers, maleate plasticizers, adipate plasticizers, carboxylate plasticizers, polycaprolactone plasticizers and plasticizers comprising modified ethylene—vinyl acetate copolymer.

Further, an ion sensor according to the invention comprises a gate insulation layer of a FET, an electrically conductive layer coating the gate insulation layer, a redox layer exhibiting a redox function coating the electrically conductive substrate, and an ion carrier membrane coating the redox layer, wherein the ion carrier membrane is sensitive to a prescribed ion and comprises polyvinyl chloride plasticized by a plasticizer, the plasticizer being selected from at least one of phthalate plasticizers, maleate plasticizers, adipate plasticizers, carboxylate plasticizers, polycaprolactone plasticizers and plasticizers comprising modified ethylene—vinyl acetate copolymer.

By virtue of this construction of the invention, the ion carrier membrane enhances the mutual stability between itself and an electrolytic polymeric layer through use of the aforementioned plasticizers, which do not readily dissolve in solution and which exhibit ionic mobility in the ion carrier membrane.

Further, the ion carrier membane is prevented from eluting into an electrolytic polymeric layer (redox layer) and the stability thereof with respect to the electrolytic polymerization layer is raised by using a plasticizer selected from polycaprolactone plasticizers and plasticizers comprising modified ethylene—vinyl acetate copolymer, which plasticizers are polymeric, do not readily dissolve in solution, plasticize polyvinyl chloride in the ion carrier membrane and are compatible with the ion carrier material.

Preferred embodiments of the invention are as follows:

(1) The weight ratio of plasticizer to polyvinyl chloride is 100-500:100.

(2) A phthalate having a carbon number of from 4 to 14, particularly di(2-ethylhexyl) phthalate (DOP), is used as the phthalate plasticizer.

(3) Dioctyl maleate (DOM) is used as the maleate plasticizer.

(4) Dioctyl adipate (DOA) is used as the adipate plasticizer.

(5) Adipate polyester is used as the adipate plasticizer.

(6) Benzophenontetracarboxylic undecylic acid (BTCU) is used as the carboxylic plasticizer.

In accordance with the invention, there can be provided an ion carrier membrane, and an ion sensor having the same, in which the ion carrier membrane is endowed with improved stability with respect to an electrolytic polymeric layer by using a plasticizer which does not readily dissolve in solution, and which exhibits ionic mobility in the ion carrier membrane.

The following results are obtained:

(1) It has been found that an ion sensor having highly stable sensor characteristics for no less than about one month can be fabricated by using DOP as the plasticizer in the PVC ion carrier membrane of the membrane-coated electrode.

(2) It has been found that a large quantity of the plasticizer which dissolves in the PVC influences the durability of the electrode (a coated wire-type electrode and ISFET electrode).

Further, according to the invention, there can be provided an ion carrier membrane, and an ion sensor having the same, in which the ion carrier membrane is prevented from dissolving and eluting in an electrolytic polymeric layer (redox layer) and is improved in stability with respect to the electrolytic polymeric layer by virtue of using a plasticizer selected from among polycaprolactone plasticizers and plasticizers comprising modified ethylene—vinyl acetate copolymer, which plasticizers do not readily dissolve in a solution under measurement, plasticize polyvinyl chloride resin in the ion carrier membrane and are compatible with the ion carrier material.

The following results are obtained:

(1) It has been found that a pH sensor having highly stable sensor characteristics for no less than about three months can be fabricated by selecting the plasticizer, which is used as the plasticizer in the PVC ion carrier membrane of the membrane-coated electrode, from among polycaprolactone plasticizers and plasticizers comprising modified ethylene—vinyl acetate copolymer. (In an acceleration test using an oven, it was found that durability could be increased more than three-fold over that obtained with the monomeric ester DOS used conventionally.)

(2) In tests for elutants and elutant toxicity, it was found that the amount of elution of the polycaprolactone plasticizers and plasticizers comprising modified ethylene—vinyl acetate copolymer was extremely small, and that the toxicity of the elutants posed no problem. This makes it possible to provide an ion sensor which can be used in blood and in both in vivo and ex vivo measurements.

BRIEF DESCRIPTION OF THE DRAWINGS

FIGS. 3(a) and 3(b) are views showing the characteristics of the membrane-coated electrodes of Examples 1 through 5;

FIGS. 6(a) and 6(b) are views showing the characteristics of a membrane-coated electrode in Example 7;

FIG. 7 is a structural view of membrane-coated electrodes fabricated in Examples 8 and 13;

FIG. 8(a) is a view showing temporal change in the sensitivity of a pH sensor fabricated in Examples 8 and 9.

BEST MODE FOR CARRYING OUT THE INVENTION

Example 1

Figure 1:
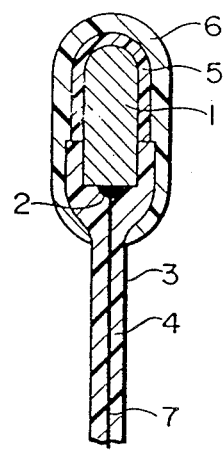
FIG. 1 is a structural view of membrane-coated electrodes fabricated in Examples 1 through 5.

The coated electrode shown in FIG. 1 was fabricated through the following procedure: A columnar member 1 having a diameter of 1.56 mm was cut from a sheet of basal plane pyrolytic graphite (BPG) (manufactured by UCC). A silver wire serving as a lead wire 7 was connected to one end of the BPG column 1 using an electrically conductive adhesive 2 (C-850-6, manufactured by Amicon K.K.). The exterior of the lead wire 7 was insulated with a heat-shrinkable tube 3, and the space between the tube 3 and the BPG 1 was insulated using a urethane adhesive 4. A redox layer 5 was formed on the surface of the BPG substrate by carrying out an electrolytic reaction, under the electrolytic conditions shown below, in a three-pole cell using the BPG substrate, fabricated as set forth above, as a working electrode, a reference electrode (a saturated sodium chloride calomel electrode, referred to as an "SSCE"), and a counter electrode (a platinum mesh).

Electrolyte: An acetonitrile solution of 0.2 M NaClO$_4$ and 0.5 M 2,6 xylenol

Electrolytic reaction conditions: The electrolyzing voltage was swept three times (sweep rate: 50 mV/sec) from 0 V to 1.5 V (vs. the SSCE), followed by carrying out constant-potential electrolysis for 10 min at 1.5 V (vs. the SSCE).

The redox layer so prepared was dark-red in color. After being washed and dried, the member fabricated above was dipped in a solution of a hydrogen ion carrier solution to form an ion carrier membrane 6 on the redox layer 5.

| Composition of hydrogen ion carrier solution: | |
|---|---|
| tridodecyl amine | 15.65 mg/ml |
| tetrakis(p-chlorophenyl) potassium borate | 1.565 mg/ml |
| di(2-ethylhexyl) phthalate (DOP) | 162.8 mg/ml |
| polyvinyl chloride (p$_n$—1050) | 81.25 mg/ml |
| tetrahydrofuran (THF) (solvent) | 10 ml |
| Dipping conditions: | |
| dipping rate: | 10 cm/min |
| number of times: | 15 times |
| carrier membrane thickness: | about 0.7 mm |

Experiment No.1

Figure 2:
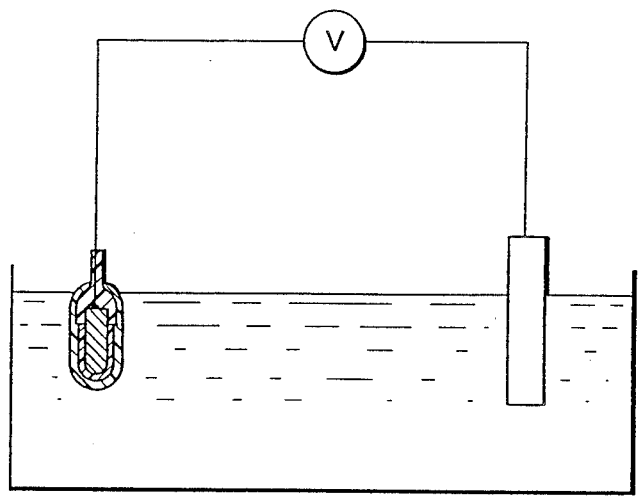
FIG. 2 is a view illustrating the membrane-coated electrode of FIG. 1 undergoing measurement.

The circuit shown in FIG. 2 was used to measure a change in the Nernst response of an electrode obtained by coating the BPG substrate fabricated in Example 1 with the electrolytic redox layer 5 and hydrogen ion carrier membrane 6. The results are as shown in Table 1.

TABLE 1

| Time (Days) | Example No. 1 Eo:Slope (mV/pH) of Nernst Equation | Example No. 2 Eo:Slope (mV/pH) of Nernst Equation |
| --- | --- | --- |
| Initial Stage | 4 days required for membrane stabilization | Same as at left |
| 4 Days | 502.83:63.04 | 508.59:62.50 |
| 7 Days | 501.26:62.63 | 501.27:62.64 |
| 18 Days | 504.22:62.89 | 492.38:60.84 |
| 25 Days | 499.56:62.56 | 485.89:60.72 |

Comparison electrode: saturated sodium chloride calomel electrode (SSCE)
Temperature at measurement: 37° C.

Example 2

A membrane-coated electrode was fabricated as in Example 1 except for the fact that dioctyl sebacate (DOS) was used instead of DOP as the plasticizer for forming the hydrogen ion carrier membrane 6 of Example 1.

Experiment No. 2

The results of measuring pH characteristics using the membrane-coated electrode of Example 1 are as shown in Table 1. About seven days were required for the reference electrode potential ($E_o$) to stabilize.

Examples 3–5

A membrane-coated electrode was fabricated as in Example 1 except for the fact that the types of plasticizer and solvent were changed, as shown in Table 2:

TABLE 2

| Example | Plasticizer | Solvent |
| --- | --- | --- |
| 3 | dioctyl adipate (DOA) | THF |
| 4 | dioctyl maleate (DOM) | THF |
| 5 | dioctyl sebacate (DOS) | cyclohexane |

Experiment Nos. 3–5

The results of measuring the durability of sensor characteristics (namely the reference electrode potential $E_o$ and slope of the Nernst equation) using the membrane-coated electrodes of Examples 3–5 are as shown in Table 3. It should be noted that results similar to those shown for Example 3 were obtained even with a carboxylic plasticizer [benzophenontetracarboxylic undecylic acid (BTCU)].

TABLE 3

| Elapsed Time | Example | 3 | 4 | 5 |
| --- | --- | --- | --- | --- |
| 4 Days | Eo | 510.36 | 484.45 | 512.36 |
|  | Slope | 62.52 | 59.55 | 62.48 |
| 7 Days | Eo | 516.2 | 487.6 | 441.2 |
|  | Slope | 62.57 | 60.57 | 56.59 |
| 18 Days | Eo | 484.7 | 491.4 | 350.6 |
|  | Slope | 59.64 | 61.43 | 45.99 |
| 25 Days | Eo | 477.2 | 487.1 | 740.2 |
|  | Slope | 59.39 | 61.22 | 49.15 |

These results show that the reference electrode potential $E_o$ and slope of the Nernst equation exhibit the best stability when the DOM-THF combination is used.

It is evident that the DOA-THF combination results in a large fluctuation in $E_o$, and that the DOS-cyclohexane combination causes a large fluctuation in both $E_o$ and the slope of the Nernst equation.

Figure 3A:
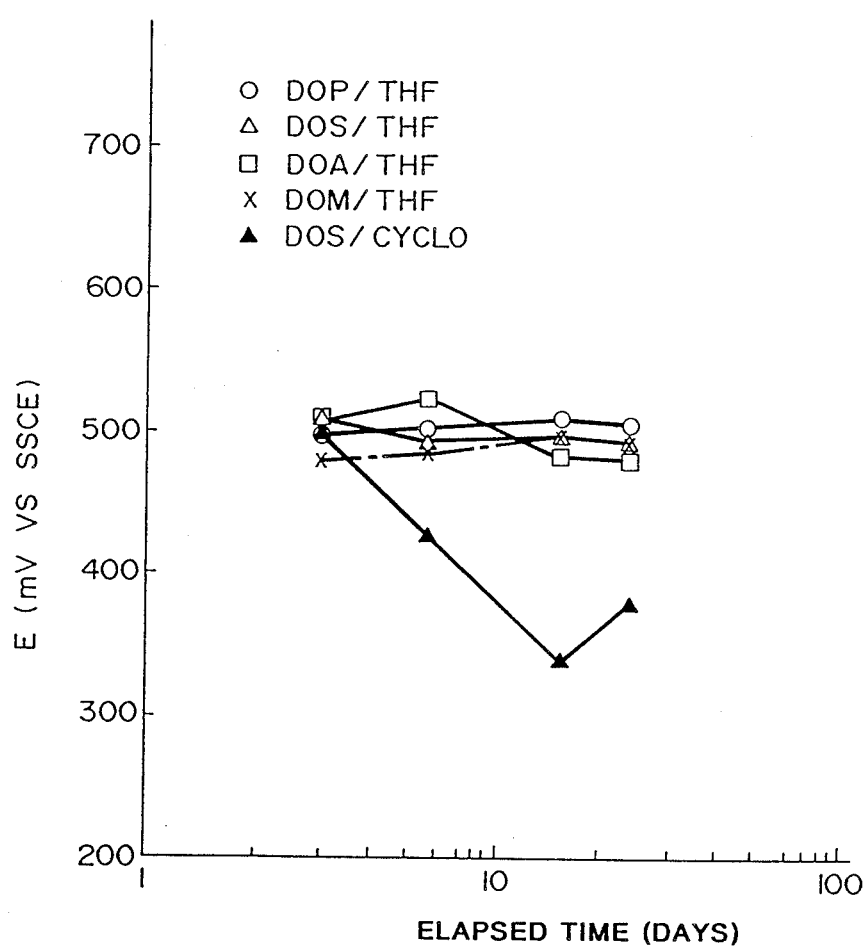

The overall results are illustrated in FIGS. 3(a) and 3(b).

Example 6

Figures 4, 5:
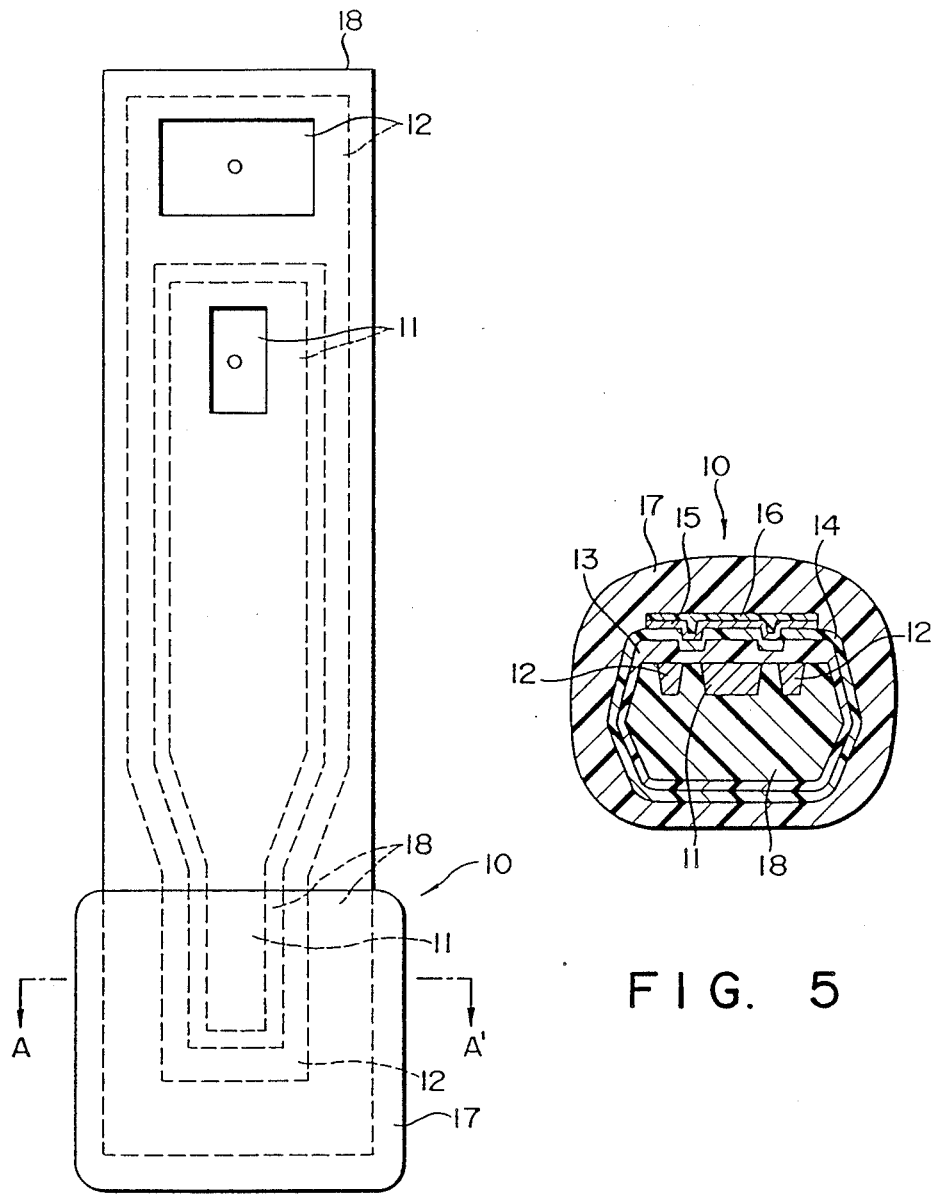
FIGS. 4 and 5 are structural views of an ion sensor fabricated in Example 6.

An electrically conductive carbon membrane 15 was formed on the surface of a gate insulation layer 14 of a MOSFET, and a redox layer 16 and hydrogen ion carrier membrane 17 were formed on the carbon membrane 15 as in Examples 1 and 7. The resulting ion sensor is illustrated in FIGS. 4 and 5. The formation of the electrically conductive carbon membrane 15 is described below.

(1) MOSFET

The MOSFET used was a FET (a so-called insulated-gate FET) having a structure in which p-type Si—$SiO_2$ gate insulation layers are formed on a p-type silicon wafer. The FET was fabricated on a p-type silicon wafer utilizing an ordinary planar technique that relies upon photolithography, and the result was coated with the insulating layer 14, consisting of silicon nitride, using a sputtering process. Numeral 11 denotes a drain, 12 a source, 13 an oxide film, and 18 a silicon substrate.

(2) Electrically conductive carbon membrane

An electrically conductive carbon membrane (membrane thickness: 2000 A) was formed as the electrically conductive layer 15 by an ion beam sputtering process on the surface of the gate insulation layer 14 of the MOSFET fabricated as described above.

Experiment No. 6

The electrode of Example 6 was tested as in Experiment No. 1 to measure its conductivity characteristics (the reference electrode potential $E_o$ and slope of the Nernst equation) and its durability. It was clarified that results similar to those seen in Example 1 are obtained, and that the durability of the electrode is improved by using DOP as the hydrogen ion carrier membrane.

Example 7

A carbon electrode was fabricated as in Example 1, and the redox layer 3 was deposited by electrolytic polymerization, as in Example 1. Though the hydrogen ion carrier membrane 4 was fabricated using a method the same as that employed in Example 1, the composition was changed to that shown in Table 4.

TABLE 4

(Hydrogen Ion Carrier Composition Adipate polyester (PN-250, manufactured by Adeka Argus K.K.) was used instead of dioctyl sebacate as the plasticizer.

| | | |
| --- | --- | --- |
| tridodecyl amine | 40 mg | 0.12 parts |
| tetrakis(p-chlorophenyl) potassium borate | 6 mg | 0.018 parts |
| polvinyl chloride | 325 mg | 100 parts |
| PN-250 | 650 mg | 200 parts |
| tetrahydrofuran solvent | 4 ml | |

Experiment No. 7

Electromotive force with respect to a comparison electrode (SSCE) was measured in a phosphate buffer solution using the pH sensor fabricated in accordance with Example 7 as the active electrode, the electromotive force was plotted against pH, and the slope and reference electrode potential $E^o$ were measured with the passage of time. For comparison purposes, the electrode fabricated in Example 2 was also subjected to measurement in the same way. The results are as shown in Table 5 and FIGS. 6(a), 6(b).

These results show that the slope of 61.8+0.5 mV/pH (37° C.) up to 30 days after fabrication closely approximates the theoretical value [61.5 mV/pH (37° C.)] for all electrodes. This indicates good stability. The reference electrode potential is also stable up to 30 days after fabrication.

TABLE 5

| Days After Fabrication | | 3 Days | 10 Days | 30 Days | 90 Days |
|---|---|---|---|---|---|
| PN-250 Electrode | Slope | −62.1 | −61.7 | −61.4 | −60.9 |
| | Eo | 478.1 | 480.2 | 479.5 | 469.8 |
| DOS Electrode | Slope | −62.5 | −61.4 | −61.7 | −60.4 |
| | Eo | 514.5 | 515.1 | 510.9 | 445.2 |

Experiment No. 8

A severity test (acceleration test) was performed using the pH sensor fabricated in accordance with Example 7. In the test, a measurement similar to that described in Experiment No. 7 was carried out in an oven at 60° C. while changing the electrode preservation conditions. The results are as shown in Table 6.

TABLE 6

| Days After Introduction to Oven | | 1 Day | 3 Days | 10 Days |
|---|---|---|---|---|
| PN-250 Electrode | Slope | −62.1 | −61.7 | −61.4 |
| | Eo | 478.1 | 480.2 | 479.5 |
| DOS Electrode | Slope | −61.5 | −61.4 | −64.8 |
| | Eo | 514.5 | 515.1 | 442.1 |

Experiment No. 9

The influence of oxygen gas was investigated using the pH sensor fabricated in accordance with Example 7.

A mixed gas of oxygen and nitrogen having a constant concentration was bubbled through a phosphate buffer solution having a pH of 7.4, and the potential of the pH sensor was measured at various partial pressures, e.g. 200 mmHg, 150 mmHg, 400 mmHg, of the oxygen gas in the solution. It was found that the variation in potential was within 2 mV for all electrodes, indicating no influence from oxygen gas.

The construction of a membrane-coated electrode in the following Examples is illustrated in the sectional view of FIG. 7.

Example 8

(1) Fabrication of electrode

A columnar member of BPG having a diameter of 1.0 mm and a length of 3.0 mm and serving as an electrically conductive substrate 21 was cut from a sheet of basal plane pyrolytic graphite (BPG) (manufactured by Union Carbide Company). One end of the BPG 21 was cut down to a diameter of 0.5 mm and a length of 1.5 mm, and a lead wire 25 (a polyethylene fluoride-coated copper wire) was bonded to this end of the substrate using an electrically conductive adhesive 22 (C-850-6, manufactured by Amicon K.K.). The other end of the columnar substrate 21 having a length of 1.50 mm was ground and polished into a hemispherical shape, with the surface area of the exposed portion being adjusted to an average value of 0.064 cm². The end of the substrate 21 having the lead wire 25 was inserted together with the lead wire 25 into a polyethylene fluoride tube 26 having an inner diameter of 0.60 mm and an outer diameter of 0.85 mm, and this end of the substrate was bonded along with the lead wire 25 within the tube using an epoxy resin adhesive (TB2067, manufactured by Three Bond Corp.), thereby insulating the lead wire. The tube 26 was then sheathed by a heat-shrinkable tube 27 to fabricate a BPG electrode.

Though such metals as platinum, gold, silver, copper, nickel and chrome and such compounds as indium oxide and iridium oxide can be used as the electrically conductive substrate in the abovementioned electrode, BPG is particularly preferred since it is not affected by oxygen in solution.

(2) Application of redox layer 23 by electrolytic polymerization

An electrolytic oxidative polymerization reaction was carried out under the following conditions using the above-described BPG electrode as a working electrode, a reference electrode (a saturated sodium chloride calomel electrode, or SSCE), and a counter electrode (a platinum mesh):

| Electrolyte: | 0.5M 2,6-dimethyl phenol |
|---|---|
| | 0.2M sodium perchlorate |
| | acetonitrile solvent |

Temperature at electrolysis: −20.0° C.

Electrolytic conditions: After the electrode potential was swept-three times from 0.0 V to 1.5 V (vs. the SSCE) at a sweep rate of 50 mV/sec), an electrolytic reaction was allowed occur at 1.5 V (vs. the SSCE) for 10 min.

As the result of this electrolytic polymerization process, an electrolytic oxidative polymer membrane of poly(2,6-xylenol) was deposited as the redox layer 23 to a thickness of about 30 microns on the exposed surface of the BPG substrate 21.

A membrane thickness of 0.1 um–1 mm is preferred, especially thickness of 20–100 um. A membrane thickness which is too great results in reduced speed of response and sensitivity, while a membrane which is too thin is readily influenced by the underlying electrically conductive substrate 21.

(3) Application of hydrogen ion carrier membrane 24

The membrane-coated electrode obtained as set forth above was dipped in a hydrogen ion carrier composition shown in Table 7 as wall allowed to dry. This operation was performed repeatedly 15 times, as a result of which a hydrogen ion carrier membrane 24 having a thickness of 1.00 mm was formed uniformly on the surface of the redox layer 23.

A membrane thickness of 0.1 um–2.0 mm is preferred, especially a thickness of 0.5–1.5 mm. A membrane thickness which is too great results in an enlarged electrode diameter, while a membrane which is too thin is poor in reproducibility.

The preferred amount of plasticizer is 100–300 parts by weight per 100 parts by weight of polyvinyl chloride, with 150–250 parts by weight being particularly preferred. Too much plasticizer will result in at least diminished sensitivity and, in particularly, reduced speed of response with regard to changes in temperature.

TABLE 7

| (Hydrogen Ion Carrier Composition) | | |
|---|---|---|
| tridodecyl amine | 40 mg | 0.12 parts |
| tetrakis(p-chlorophenyl) potassium borate | 6 mg | 0.018 parts |
| polyvinyl chloride | 325 mg | 100 parts |
| polycaprolactone plasticizer | 650 mg | 200 parts |
| tetrahydrofuran solvent | 4 ml | |

A polycaprolactone plasticizer was used as the plasticizer.

Example 9

(1) An electrode was fabricated as in Example 8, and (2) the redox layer was deposited by electrolytic polymerization, as in Example 8.

(3) Application of hydrogen ion carrier membrane

Though a hydrogen ion carrier membrane was fabricated using a method the same as that employed in Example 8, the composition was changed to that shown in Table 4.

TABLE 8

| (Hydrogen Ion Carrier Composition) | | |
|---|---|---|
| tridodecyl amine | 40 mg | 0.12 parts |
| tetrakis(p-chlorophenyl) potassium borate | 6 mg | 0.018 parts |
| polyvinyl chloride | 325 mg | 100 parts |
| Ervaroi 742 | 650 mg | 200 parts |
| tetrahydrofuran solvent | 4 ml | |

Modified EVA (Ervaroi 742, manufactured by Mitsui Polychemicals K.K.) was used instead of polycaprolactone as the plasticizer.

Example 10

(1) Fabrication of electrode

Instead of BPG, a graphite carbon material EG-51 (manufactured by Nippon Carbon K.K.) was used as the electrically conductive substrate to fabricate an EG-51 electrode through the same procedure employed in Example 8.

(2) The application of the redox layer 23 by electrolytic polymerization was performed as in Example 8.

(3) The application of the hydrogen ion carrier membrane 24 was performed as in Example 8 using the polycaprolactone plasticizer.

Example 11

(1) Fabrication of electrode

Instead of BPG, a graphite carbon material T-5 (manufactured by IBIDEN K.K.) was used as the electrically conductive substrate to fabricate a T-5 electrode through the same procedure employed in Example 8.

(2) The application of the redox layer 23 by electrolytic polymerization was performed as in Example 8.

(3) The application of the hydrogen ion carrier membrane 24 was performed as in Example 10.

Example 12

(1) Fabrication of electrode

Instead of BPG, a carbon material, namely the core of an automatic pencil, was used as the electrically conductive substrate to fabricate pencil-core electrode through the same procedure employed in Example 8.

(2) The application of the redox layer 23 by electrolytic polymerization was performed as in Example 8.

(3) The application of the hydrogen ion carrier membrane 24 was performed as in Example 11.

Experiment No. 10

Figure 8B:
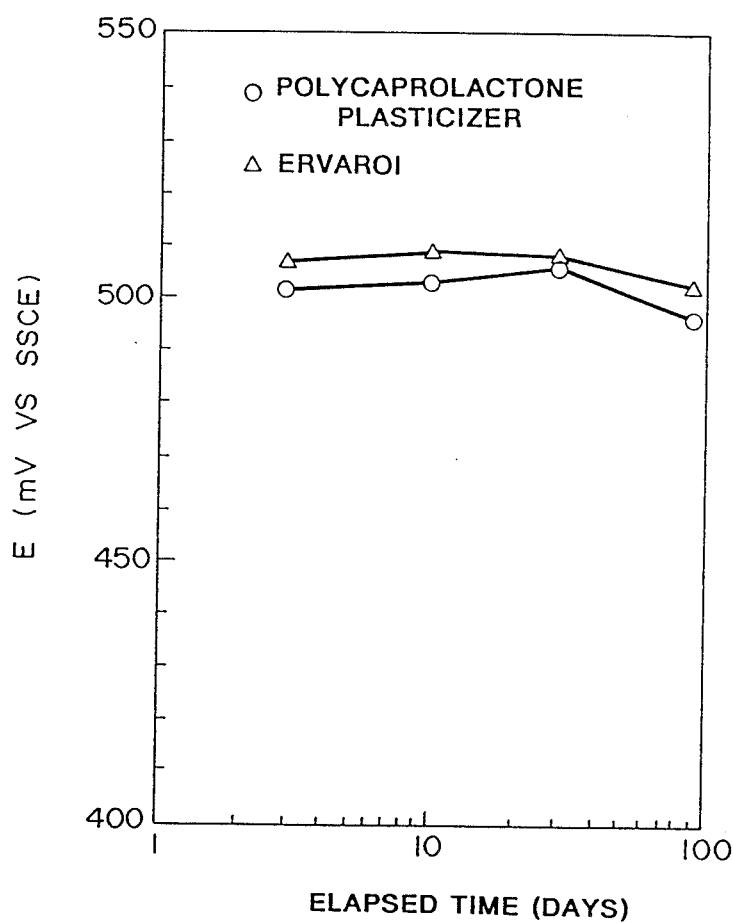
FIG. 8(b) is a view showing temporal change in the $E^o$ of a pH sensor fabricated in Examples 8 and 9.

Electromotive force with respect to a comparison electrode (SSCE) was measured in a phosphate buffer solution using the pH sensor fabricated in accordance with Example 9 as the working electrode, the electromotive force was plotted against pH, and the slope and reference electrode potential $E_o$ were measured with the passage of time. For comparison purposes, the electrode fabricated in Example 1 was also subjected to measurement in the same way. The results are as shown in Table 9 and FIGS. 8(a), 8(b).

TABLE 9

| Days After Fabrication | | 3 Days | 10 Days | 30 Days | 90 Days |
|---|---|---|---|---|---|
| Polymeric (Polycaprolactone) Plasticizer Electrode | Slope | −61.3 | −61.6 | −61.4 | −60.9 |
| | Eo | 501.4 | 503.2 | 505.9 | 495.8 |
| Ervaroi 742 Electrode | Slope | −62.5 | −62.5 | −62.7 | −62.3 |
| | Eo | 507.2 | 508.9 | 507.5 | 502.5 |

These results show that the slope of 61.8+0.5 mV/pH (37° C.) up to 30 days after fabrication closely approximates the theoretical value [61.5 mV/pH (37° C.)] for all electrodes. This indicates good stability. The reference electrode potential was also stable up to 30 days after fabrication. More than thirty days after fabrication, however, the reference electrode potential began to drop. After 90 days, the reference electrode potential dropped by 60 mV in comparison with the stable period. The electrode of the present example using the polymeric plasticizer in order to prevent the outflow of the redox layer into the plasticizer exhibited a change in reference electrode potential within +10 mV, even after 90 days. This fact demonstrates that the outflow of the redox layer into the plasticizer is prevented, thereby extending durability.

Experiment No. 11

A severity test (acceleration test) was performed using the pH sensor fabricated in accordance with Example 9. In the test, a measurement similar to that described in Experiment No. 10 was carried out in an oven at 60° C. while changing the electrode preservation conditions. The results are as shown in Table 10.

TABLE 10

| Days After Introduction to Oven | | 1 Day | 3 Days | 10 Days |
|---|---|---|---|---|
| polycaprolactone Plasticizer Electrode | Slope | −62.3 | −61.6 | −61.4 |
| | Eo | 501.4 | 503.2 | 505.9 |
| Ervaroi 742 Electrode | Slope | −62.1 | −62.4 | −61.9 |
| | Eo | 507.7 | 509.2 | 507.1 |

From the fact that the slope and reference electrode potential associated with the electrode using the polymeric plasticizer were not found to exhibit changes in excess of ±0.5 mV/pH and ±10 mV, respectively, ten days after introduction to the oven, it was confirmed that elution of the redox layer was prevented.

Experiment No. 12

Upon conducting an experiment the same as that of Experiment No. 10 using pH sensors fabricated in accordance with Examples 10, 11 and 12, it was found that the pH sensors responded linearly in close approximation to the theoretical slope, with respect to a variation in pH, even when the carbon substrate was changed. In addition, when the polycaprolactone polymeric plasticizer was used as the plasticizer, the elution of the redox layer could be prevented and durability was improved. Thus, results similar to those seen in Experiment No. 10 were obtained.

Experiment No. 13

The influence of oxygen gas was investigated using the pH sensors fabricated in accordance with Examples 8, 9, 10, 11 and 12.

A mixed gas of oxygen and nitrogen having a constant concentration was bubbled through a phosphate buffer solution having a pH of 7.4, and the potential of the pH sensor was measured at various partial pressures, e.g. 200 mmHg, 150 mmHg, 400 mmHg, of the oxygen gas in the solution. It was found that the variation in potential was within 2 mV for all electrodes, indicating no influence from oxygen gas.

Example 13

An electrically conductive carbon membrane 15 was formed on the surface of a gate insulation layer 14 of a MOSFET, and a redox layer 16 and hydrogen ion carrier membrane 17 were formed on the carbon membrane 15 as in Example 8. The structure of the resulting ion sensor was the same as that shown in FIGS. 4 and 5. The formation of the electrically conductive carbon membrane 15 is described below.

(1) MOSFET

The MOSFET used was a FET (a so-called insulated-gate FET) having a structure in which p-type Si—SiO$_2$ gate insulation layers are formed on a p-type silicon wafer. The FET was fabricated on a p-type silicon wafer utilizing an ordinary planar technique that relies upon photolithography, and the result was coated with the insulating layer 14, consisting of silicon nitride, using a CVD (chemical vapor deposition) process. Numeral 11 denotes a drain, 12 a source, 13 an oxide film, and 18 a silicon substrate.

(2) Electrically conductive carbon membrane

The electrically conductive carbon membrane 15 was formed by an ion beam sputtering process to a thickness of 2000 Å on the surface of the gate insulation layer 14 of the MOSFET fabricated as described above.

Experiment No. 14

The electrode of Example 13 was tested as in Experiment No. 10 to measure its conductivity characteristics (the reference electrode potential E$_o$ and slope of the Nernst equation) and its durability. It was clarified that results similar to those seen in Example 8 are obtained, and that the durability of the electrode is improved by using a polycaprolactone polymer as the plasticizer of the hydrogen ion carrier membrane.

Thus, as will be understood from the foregoing Examples, the pH electrodes of these Examples using a polymeric plasticizer prevent the elution of the redox layer, exhibit excellent stability and durability and are not affected by oxygen gas. In addition, the 95% speed of response was rapid, being within four seconds.

The polymeric plasticizers used herein have the following structures:

polycaprolactone polymer:
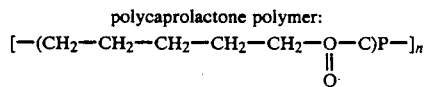

where P is the modified portion

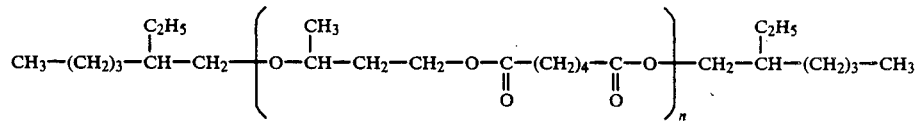

Modified EVA: Ervaroi 742:
(ethylene, carbon monoxide, vinyl acetate copolymer)

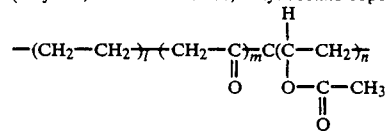

Though the foregoing examples have been described using a hydrogen ion carrier membrane as a typical ion carrier membrane, similar effects are obtained with other ion carrier membranes as well. Furthermore, the electrically conductive substrates and electrically conductive layers are not limited to carbon; metals such as gold, platinum and nickel can also be used. As for the carbon, that having a graphite-type crystal structure is preferred for use. In addition, the structures of the membrane-coated electrodes and FET sensors are not limited to those described in the Examples.

We claim:

1. An ion carrier membrane sensitive to a prescribed ion and comprising polyvinyl chloride plasticized by a plasticizer,
   said plasticizer being benzophenonetetracarboxylic undecylic acid (BTCU).

2. An ion sensor comprising an electrically conductive substrate, a redox layer exhibiting a redox function coating said electrically conductive substrate, and an ion carrier membrane coating said redox layer,
   wherein said ion carrier membrane is sensitive to a prescribed ion and comprises polyvinyl chloride plasticized by a plasticizer,
   said plasticizer being benzophenontetracarboxylic undecylic acid (BTCU).

3. An ion sensor comprising a gate insulation layer of a FET, an electrically conductive layer coating said gate insulation layer, a redox layer exhibiting a redox function coating said electrically conductive layer, and an ion carrier membrane coating said redox layer,
   wherein said ion carrier membrane is sensitive to a prescribed ion and comprises polyvinyl chloride plasticized by a plasticizer,
   said plasticizer being benzophenontetracarboxylic undecylic acid (BTCU).

* * * * *